(12) United States Patent
Lee et al.

(10) Patent No.: US 9,879,296 B2
(45) Date of Patent: Jan. 30, 2018

(54) METHOD FOR PREPARING TAGATOSE FROM RESIDUE AFTER EXTRACTING COFFEE

(71) Applicant: CJ CHEILJEDANG CORPORATION, Seoul (KR)

(72) Inventors: Young Mi Lee, Bucheon-si (KR); Seong Bo Kim, Seoul (KR); Min Hae Kim, Incheon (KR); Sung Jae Yang, Gwangmyeong-si (KR); Seung Won Park, Yongin-si (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 15/100,284

(22) PCT Filed: Nov. 27, 2014

(86) PCT No.: PCT/KR2014/011507
§ 371 (c)(1),
(2) Date: May 27, 2016

(87) PCT Pub. No.: WO2015/080501
PCT Pub. Date: Jun. 4, 2015

(65) Prior Publication Data
US 2017/0002391 A1    Jan. 5, 2017

(30) Foreign Application Priority Data

Nov. 29, 2013 (KR) .................. 10-2013-0147652

(51) Int. Cl.
C12P 19/24 (2006.01)
C12P 19/02 (2006.01)
C12N 9/90 (2006.01)

(52) U.S. Cl.
CPC ............. *C12P 19/24* (2013.01); *C12N 9/90* (2013.01); *C12P 19/02* (2013.01); *C12Y 503/01003* (2013.01)

(58) Field of Classification Search
None
See application file for complete search history.

(56) References Cited

U.S. PATENT DOCUMENTS

| 6,991,923 | B2 | 1/2006 | Bertelsen et al. |
| 8,765,427 | B2 * | 7/2014 | Murata ............ C12P 7/06 435/162 |
| 9,416,375 | B2 * | 8/2016 | Fernholz ............ A01N 37/16 |

FOREIGN PATENT DOCUMENTS

| KR | 10-2004-0102813 A | 12/2004 |
| KR | 10-2008-0090777 A | 10/2008 |
| KR | 10-2010-0016948 A | 2/2010 |
| WO | 2008/066260 A1 | 6/2008 |

OTHER PUBLICATIONS

Vardon et al. (ACS Sustainable Engin., vol. 1 (10), pp. 1286-1294, Aug. 2, 2013).*
Torres et al. (Molecules, 22 (284), pp. 1-15, 2017).*
Martinez-Saez et al. (Food Chem., vol. 216, 2017, pp. 114-122).*
International Search Report dated Mar. 5, 2015 of PCT/KR2014/011507 which is the parent application and its English translation—4 pages.
Notice of Allowance dated Jan. 26, 2015 for Korean Patent Application No. 10-2013-0147652—1 page.
European Search Report dated Jun. 29, 2017 of corresponding European Patent Application No. 14865999.8—11 pages.
Yoon et al., "Properties of L-arabinose isomerase from *Escherichia coli* as biocatalyst for tagatose production", World Journal of Microbiology & Biotechnology, 2003, vol. 19, pp. 47-51.
Mussatto et al., "A Study on Chemical Constituents and Sugars Extraction from Spent Coffee Grounds," Carbohydrate Polymers, 2011, vol. 83, pp. 368-374.

* cited by examiner

*Primary Examiner* — Hope Robinson
(74) *Attorney, Agent, or Firm* — Knobbe Martens Olson & Bear LLP

(57) ABSTRACT

The present invention relates to a method for preparing tagatose from residue after extracting coffee, comprising: obtaining a hydrolysate by hydrolyzing residue after extracting coffee into acid; obtaining a hydrolysate refined by decolorization and ion-refining the obtained hydrolysate; and obtaining tagatose by isomerizing the refined hydrolysate to an arabinose isomerase.

20 Claims, 2 Drawing Sheets

METHOD FOR PREPARING TAGATOSE FROM RESIDUE AFTER EXTRACTING COFFEE

TECHNICAL FIELD

Embodiments of the invention relate to a method for preparing tagatose from spent coffee grounds.

BACKGROUND TECHNOLOGY

Tagatose is a naturally occurring ketohexose and has a natural sweet taste (sweetness: 92% as sweet as sucrose) which is hardly distinguishable from sucrose and physical properties similar to sucrose. In addition, tagatose has various healthy and functional characteristics (low-calorie, antidiabetic and prebiotic effects, prevention of dental caries), and thus has been used in various products, for instance, drinks (low-calorie, supplement to bitter taste of high potency sweeteners, or reduction of blood glucose level after meal), particularly coffees (low-calorie, reduction of blood glucose level after meal, flavor enhancement), ice creams, chocolates, candies (low-calorie, non-inducing dental caries, flavor enhancement), dietary foods (low-calorie or reduction of blood glucose level after meal), foods for patients (controlling blood glucose level after meal and fasting blood glucose level, or low-calorie), and the like. In this regard, tagatose is an alternative sweetener capable of satisfying both taste and health.

However, tagatose is not often found in nature and is a rare sugar present only in small amounts in dairy products and some fruits. In order to use tagatose as a functional sweetener, it is essential to develop a method for mass production of tagatose from inexpensive raw materials.

Tagatose can be produced from galactose by enzymatic isomerization or chemical isomerization. Galactose as a substrate is a naturally occurring monosaccharide which exists in relatively small amounts, and serves as a basic constitutional unit for hydrocarbons of organisms. Typical examples of hydrocarbon components containing galactose include lactose, soybean oligosaccharides (stachyose, raffinose), agar, guar gum, arabinogalactan (consisting of few D-galactose molecules having a backbone of β-1,3 linkages with side chains of one or two L-arabinose molecules at the 6 residue), galactomannan (one of complex polysaccharides consisting of a mannose backbone of (1,4)-linkages with side chains of galactose having a 1,6-linkage), and the like. However, the preparation of tagatose by directly taking various galactose-containing hydrocarbon sources from nature is uneconomical.

Therefore, there is a high need for a more economical and efficient method for preparing tagatose.

DISCLOSURE

Technical Problem

Embodiments of the invention provide a method for preparing tagatose by preventing resource waste by means of recycling wastes and reducing production costs, thereby providing consumers with low cost tagatose.

Embodiments of the invention provide a method for preparing tagatose economically and at high productivity as compared to typical methods for preparing tagatose.

Technical Solution

One embodiment of the present invention provides a method for preparing tagatose from spent coffee grounds, including:

subjecting spent coffee grounds to hot water extraction to obtain a hot water extract, hydrolyzing the hot water extract with an acid to obtain a hydrolysate, decolorization and ion-refining the resulting hydrolysate to obtain a refined hydrolysate, and isomerizing the refined hydrolysate with an L-arabinose isomerase to obtain tagatose.

Another embodiment of the present invention provides a method for preparing tagatose from spent coffee grounds, including:

subjecting the spent coffee grounds to acid hydrolysis to obtain a hydrolysate, decolorization and ion-refining the resulting hydrolysate to obtain a refined hydrolysate, and isomerizing the refined hydrolysate with an L-arabinose isomerase to obtain tagatose.

A further embodiment of the present invention provides a method for preparing tagatose from spent coffee grounds, including:

preparing galactose from spent coffee grounds, and isomerizing galactose using an L-arabinose isomerase to obtain tagatose.

Advantageous Effects

The present invention can provide a method for preparing tagatose capable of preventing resource waste and reducing production costs by recycling spent coffee grounds as a raw material for tagatose instead of discarding as waste, thereby providing consumers with low cost tagatose.

The present invention can provide a method for preparing tagatose economically and with high productivity as compared to typical methods for preparing tagatose.

EMBODIMENTS

Figure 1:
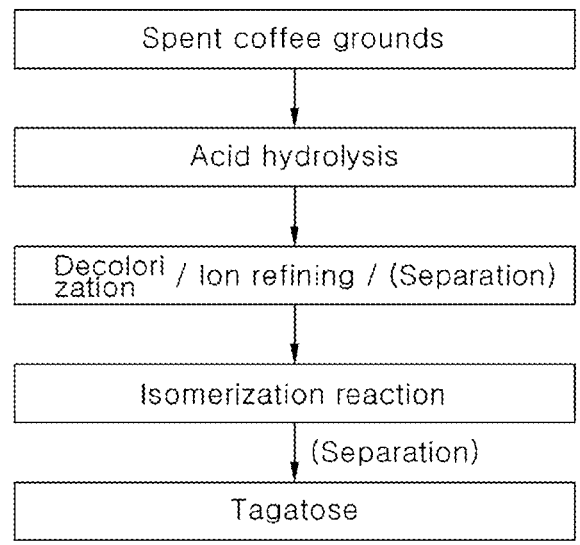
FIG. 1 is a flowchart of a method for preparing tagatose in accordance with one embodiment of the invention.
Figure 2:
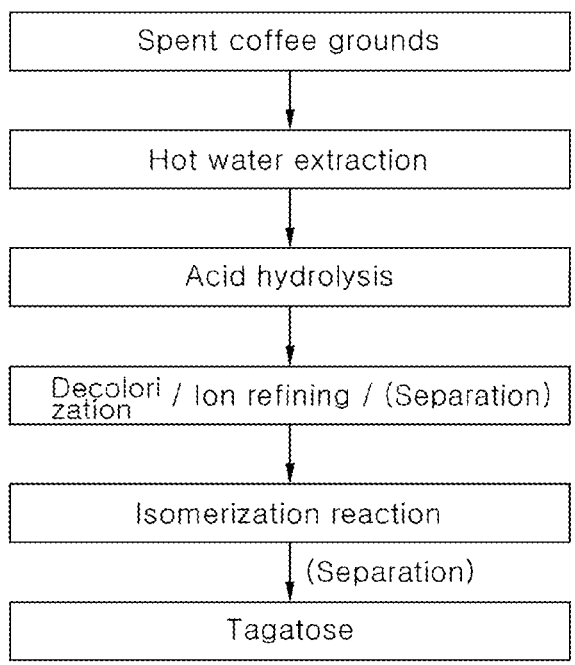
FIG. 2 is a flowchart of a method for preparing tagatose in accordance with another embodiment of the invention. The separation procedure after decolorization/ion refining in FIGS. 1 and 2 refers to separation of galactose from the refined hydrolysate by, for example, chromatography, and the separation procedure after isomerization in FIGS. 1 and 2 refers to separation of tagatose from the isomerized mass after isomerization. These separation procedures can be omitted and are indicated in parenthesis.

Hereinafter, embodiments of the invention will be described in more detail. Descriptions of details apparent to those skilled in the art having ordinary knowledge in this technical field or relevant field will be omitted herein.

In accordance with one aspect of the present invention, a method for preparing tagatose from spent coffee grounds, includes:

hydrolyzing the spent coffee grounds to obtain a hydrolysate, decolorization and ion-refining the resulting hydrolysate to obtain a refined hydrolysate, and isomerizing the refined hydrolysate with an L-arabinose isomerase to obtain tagatose.

According to embodiments of the invention, coffee ground waste can be used as a raw material for preparing galactose or tagatose. Waste coffee grounds refer to residues of coffee, for example, coffee waste after brewing coffee beans. Some spent coffee grounds are used as organic fertilizers and most spent coffee grounds are incinerated or buried like general waste. The inventors of the present invention have found that such spent coffee grounds can be recycled as a raw material for preparing galactose or tagatose.

Content of arabinose in spent coffee grounds is less than 10 wt % (% by weight), specifically less than 8.5 wt %, more specifically less than 8.0 wt %, based on the weight of saccharides in the corresponding spent coffee grounds. Within this range of arabinose, it is advantageous in terms of improvement in tagatose productivity by an L-arabinose isomerase. Currently, byproducts generated in production processes using large amounts of plant bodies containing various kinds of proteins, fatty acids and saccharide components as raw materials, for example, isolated soybean protein byproducts or defatted rice bran extract residues and the like can contain galactose, as shown in the following Table 1 (wt % of each process byproduct based on the weight of saccharides).

TABLE 1

Saccharide component ratio (%) per process byproduct

| | Glucose | Xylose | Galactose | Arabinose | Mannose |
|---|---|---|---|---|---|
| Spent coffee grounds | 23.1 | 0.9 | 24.7 | 6.1 | 45.1 |
| Isolated soybean protein byproduct | 7.8 | 12.7 | 50.6 | 28.9 | 0.0 |
| Defatted rice bran extract residue | 51.3 | 20.3 | 19.9 | 8.5 | 0.0 |

The enzyme used in preparation of tagatose (enzymatic isomerization method) is an L-arabinose isomerase, which has activity of not only converting D-galactose into D-tagatose but also converting L-arabinose as a reaction substrate into L-ribulose. Substrate specificity of an L-arabinose isomerase for L-arabinose appears to be higher than that of an L-arabinose isomerase for D-galactose. Reaction specificity for glucose, mannose, and xylose was found to be very low, causing low reactivity. As shown in Table 2, in reaction of the L-arabinose isomerase, the arabinose content listed in Table 2 is added, followed by checking tagatose production ratio. As a result, it could be seen that the production ratio of tagatose decreases with increasing content of arabinose.

TABLE 2

Tagatose production ratio (%) depending on arabinose content in galactose substrate for isomerase

| Galactose:Arabinose weight ratio | Tagatose production ratio (wt %) |
|---|---|
| (100:0) | 100 |
| (90:10) | 98.2 |
| (80:20) | 97.1 |
| (50:50) | 89.8 |

When byproducts with high arabinose content such as isolated soybean protein byproducts or defatted rice bran extract residues are used as raw materials in the preparation of tagatose, efficiency of preparing tagatose can be reduced due to the high content of arabinose.

Thus, spent coffee grounds utilizable in the present invention contains arabinose in an amount of less than 10 wt %, specifically less than 8.5 wt %, more specifically less than 8.0 wt %, and galactose in an amount of 20 wt % or more, specifically 23 wt % or more, based on the weight of saccharides in the spent coffee grounds.

Use of spent coffee grounds as raw materials for preparing tagatose provides the following further advantages.

Firstly, spent coffee grounds obtained from roasted coffee beans can have antimicrobial properties. Spent coffee grounds obtained from roasted coffee beans include small amounts of substances which inhibit growth of food derived pathogenic bacteria related to food toxicity such as *Salmonella*, *E.coil* O157:H7, *Staphylococus aureus*, potency of which is strong. In addition, spent coffee grounds obtained from roasted coffee beans have low protein and fat contents as compared to other plant derived byproducts (for example, isolated soybean protein byproducts and the like), which can improve storage stability.

Secondly, spent coffee grounds do not pose genetically modified organism (GMO) related issues to raw materials. Currently, due to production cost rise according to reduction in cultivated land, shortage in agriculture labor, and cost increase in inputs, genetically recombinant agricultural products such as soybeans and rice (seed) are commercially purchased. However, the use of these genetically recombinant agricultural products as raw materials has raised a question regarding harmfulness on human health and the environment. On the contrary, unlike soybean byproducts and the like, the use of coffee byproducts would not cause such controversy.

Thirdly, spent coffee grounds do not contain food allergens. Allergens as causative agents for food allergy are mostly proteins. Examples of causative foods for allergy may include soybeans, milk, nuts, and the like. For example, isolated soybean protein byproducts or whey byproducts containing galactose cannot be said to be safe against allergic reaction. However, spent coffee grounds are safe to such reaction. In addition, spent coffee grounds contain antioxidants, which can provide an effect of enhancing an immune system.

In the method for preparing tagatose according to one embodiment of the present invention, firstly, spent coffee grounds are subjected to hot water extraction to obtain a hot water extract. The hot water extract is obtained by extracting oligosaccharide components (for example: arabinogalactan, galactomannan, and the like) contained in spent coffee grounds. The hot water extract liquid may be water, distilled water or saline, specifically water (for example, tap water). The hot water extraction may be performed by adding water in amounts of 2 to 6 times the weight of spent coffee grounds, and then maintaining the mass at 25° C. to 180° C. for 1 hour to 24 hours. Under the extraction conditions, oligosaccharides contained in spent coffee grounds can be extracted in high yield. Specifically, hot water extraction may be performed by adding water in amounts of 3 to 5 times the weight of spent coffee grounds, and then maintaining the mass at 125° C. to 180° C. for 1 hour to 12 hours. More specifically, the hot water extraction may include heating the reaction mass at 125° C. to 180° C. for 1 hour to 6 hours. In particular, heating may be performed at 150° C. to 180° C. for 2 hour to 4 hours. The yield and content of the extract tend to increase to a certain level, as the extraction temperature and extraction time increase. For example, when extraction is performed at 150° C. for 3 hours or at 160° C. for 1 hour, an extraction yield of 95% or more can be obtained. When extraction is performed at a temperature of higher than 160° C., the extraction yield tends to remain almost constant. The hot water extraction procedure may be optionally omitted. Namely, spent coffee grounds may be subjected to acid hydrolysis without being subjected to hot water extraction.

Next, the hot water extract may be subjected to acid hydrolysis to obtain hydrolysates. Although the hot water extract per se may also be used, the hot water extract may be subjected to acid hydrolysis after concentration in order to increase saccharide contents and reduce production costs through reduction in reaction facilities. The concentration may be performed such that the oligosaccharide content in the hot water extract is greater than 20 wt %.

Acid hydrolysis may be performed by hydrolyzing oligosaccharides (for example: arabinogalactan, galactomannan, and the like) in oligosaccharide saccharified liquid so as to obtain galactose. The acid may be used without limitation so long as the acid can hydrolyze oligosaccharides. Examples of acids may include hydrochloric acid, sulfuric acid, and nitric acid. Considering the hydrolysis rate depending on concentration of acids, hydrochloric acid is preferable. The amount of acids added is 0.25 wt % to 10 wt % (wt/v %), specifically 0.25 wt % to 5 wt %, more specifically 0.5 wt % to 3 wt %, based on the total volume of the hot water extract. The hydrolysis rate may differ depending on the kinds of acids. For example, for hydrochloric acid, the hydrolysis rate may be about 97% or more in a concentration of 1 wt % or more. For sulfuric acid, the hydrolysis rate may be about 97% or more in a concentration of 3 wt % or more. The hydrolysis conditions may include reaction at 100° C. to 150° C. for 1 minute to 6 hours after acid addition. In order to collect soluble materials dissolved in an aqueous layer after the hydrolysis procedure, a basic material such as calcium carbonate is added to the aqueous layer to adjust pH to 6 or more, followed by leaving the resulting mass at room temperature, thereby obtaining a reaction precipitate of the acid and the base.

In accordance with another aspect of the present invention, a method for preparing tagatose from spent coffee grounds includes:

hydrolyzing spent coffee grounds with an acid to obtain a hydrolysate, decolorization and ion-refining the resulting hydrolysate to obtain a refined hydrolysate, and isomerizing the refined hydrolysate with an L-arabinose isomerase to obtain tagatose.

As set forth above, spent coffee grounds may be subjected to acid hydrolysis without hot water extraction, thereby obtaining hydrolysates. The direct acid hydrolysis of spent coffee grounds may be performed by adding water in amounts of 1 to 7 times the weight of spent coffee grounds, specifically 2 to 6 times, more specifically about 4 times.

In the above aspect, in order to hydrolyze oligosaccharides (for example, arabinogalactan, galactomannan, and the like) contained in the oligosaccharide saccharified liquid, acid hydrolysis is performed to produce galactose. The acid may be used without limitation so long as the acid can hydrolyze oligosaccharides. Examples of acids may include hydrochloric acid, sulfuric acid, and nitric. Hydrochloric acid is preferable in terms of the hydrolysis rate depending on concentration of acids. The amount of acids added is 0.25 wt % to 10 wt % (wt/v %), specifically 0.25 wt % to 5 wt %, more specifically 0.5 wt % to 3 wt %, based on the total volume of spent coffee grounds to which water is added. The hydrolysis rate may differ depending on the kinds of acids. For example, for hydrochloric acid, the hydrolysis rate is about 95% or more in a concentration of 0.5 wt % or more. For sulfuric acid, the hydrolysis rate is about 97% or more in a concentration of 1 wt % or more. The hydrolysis conditions may include reaction at 100° C. to 150° C. for 1 minute to 6 hours after acid addition. In order to collect soluble materials dissolved in an aqueous layer after the hydrolysis process, a basic material such as calcium carbonate is added to adjust pH to 6 or more, and left at room temperature, thereby producing precipitates of the acid and the base.

Next, the obtained hydrolysates are subjected to decolorization and ion refining to obtain refined hydrolysates. The decolorization procedure may include adding 0.1 wt % to 5.0 wt % (wt/v %) of activated carbon to the total volume of the hydrolysates and reacting the mass at 15° C. to 100° C., specifically at 25° C. to 75° C. The decolorization procedure may be further performed at a stirring speed of 10 rpm to 1000 rpm, specifically 10 rpm to 100 rpm for 5 minutes to 6 hours, specifically 30 minutes to 3 hours. Next, ion refining may be performed using cation exchange resins, anion exchange resins, or both cation/anion exchange resins. Through the decolorization and ion refining procedures, impurities such as color materials and ionic materials contained in the hydrolysates can be removed.

The cation exchange resins are polymers having an acidic group and capable of exchanging cations such as hydrogen ions or metal ions. The anion exchange resins are polymers having a basic group and capable of exchanging ammonium groups with anions such as hydroxyl ions or halogen ions. In the present invention, it is possible to use one or more of the cation exchange resins or the anion exchange resins. In order to effectively remove ionic materials, it is possible to use cation exchange resins and anion exchange resins at the same time. In this case, the ratio of the cation exchange resins to the anion exchange resins may range from 1:1 to 1:3, specifically, from 1:1.5 to 1:2. After ion refining, the content of ionic materials in the hydrolysates may be 10 microsiemens per centimeter upon measurement using an electrical conductivity meter.

The hydrolysates from which impurities such as color materials, ionic materials and the like are removed through the decolorization and ion refining procedures may be further concentrated for subsequent reactions. For example, the hydrolysates may be concentrated 30% or more (g/g solution), specifically 40% or more, more specifically 50% or more.

The refined hydrolysates or the further concentrated hydrolysates may be subjected to chromatography to separate pure galactose, which in turn is used in isomerization, or may be directly subjected to isomerization without chromatographic separation in order to minimize the number of production steps. In the case of separating galactose, the refined hydrolysate may be subjected to ion exchange resins having calcium groups (Amberlite CR1310 Ca), followed by eluting the resulting fraction with deionized water, and then separated by chromatography to obtain a refined galactose solution.

Next, the refined hydrolysate is isomerized by an L-arabinose isomerase to obtain tagatose. The L-arabinose isomerase may be an L-arabinose isomerase derived from hyperthermophiles, for example, *Thermotoga neapolitana*. The isomerization may include reacting the refined hydrolysate together with a strain expressing L-arabinose isomerase or in the presence of L-arabinose isomerase at a temperature ranging from 40° C. to 90° C. for 1 hour to 12 hours, specifically at about 50° C. to 80° C. for 1 hour to 6 hours. The isomerase is capable of producing tagatose using galactose contained in the refined saccharified liquid. The strain capable of expressing L-arabinose isomerase is a transformed *Corynebacterium glutamicum*, specifically *Corynebacterium glutamicum* KCCM10786P, which was deposited at the Korea Culture Center of Microorganisms on Oct. 18, 2006.

The preparation method according to the embodiment may further include isomerizing galactose with an L-arabinose isomerase, and refining the resulting reaction product by chromatography to separate tagatose.

In accordance with a further aspect of the present invention, a method for preparing tagatose from spent coffee grounds includes:

preparing galactose from spent coffee grounds, and isomerizing galactose with an L-arabinose isomerase to obtain tagatose.

EXAMPLES

Hereinafter, the present invention will be described in more detail with reference to the following examples, comparative examples and experimental examples. It should be understood that these examples are provided for illustration only and are not to be in any way construed as limiting the present invention.

Example 1

Analysis of Saccharide Component in Spent Coffee Grounds

In order to evaluate galactose content in spent coffee grounds of commercially available coffee beans, samples of spent coffee grounds were collected from several companies, followed by evaluating saccharide content by high performance liquid chromatography (HPLC). HPLC was performed by injecting test samples into a column (SUPELCOGEL™ Pb column) set to 80° C. and flowing through the column using distilled water as a mobile solvent at a rate of 0.3 ml/min. The results of saccharide analysis are shown in Table 3. It could be seen that coffee beans and spent coffee grounds contain saccharides in the form of galactomannan and arabinogalactan.

TABLE 3

Saccharide ratio (%) for spent coffee grounds available from companies

| | Glucose | Xylose | Galactose | Arabinose | Mannose |
|---|---|---|---|---|---|
| Spent coffee grounds_available from company A | 23.14 | 0.92 | 24.68 | 6.11 | 45.15 |
| Spent coffee grounds_available from company B | 26.58 | — | 24.51 | 4.12 | 44.79 |
| Spent coffee grounds_available from company C | 27.18 | — | 26.58 | 5.40 | 40.85 |

Example 2

Hot Water Extraction of Oligosaccharides from Spent Coffee Grounds

Spent coffee grounds available from company B, which were shown to have relatively low content of arabinose in Example 1, were subjected to extraction in order to increase extraction yield of coffee oligosaccharides. Extraction was carried out by changing extraction conditions such as liquid-to-solid ratio, extraction temperature, extraction time, and the like.

Example 2-1

Selection of Amount of Added Water in Spent Coffee Grounds (Liquid-to-solid Ratio)

Extraction was performed by adding water in amounts of 20 g, 40 g, and 40 g to 10 g of spent coffee grounds. In the case of adding 20 g of water, since spent coffee grounds absorbed water and thus reduced the recovery amount of liquid, oligosaccharide recovery yield was low. In the case of adding 60 g of water, saccharide concentration was too diluted. Thus, 40 g of water was added to 10 g of spent coffee grounds.

Example 2-2

Extraction Depending on Extraction Temperature and Extraction Time

Hot water extraction was performed at a liquid-to-solid ratio selected in Example 2-1, namely, by changing extraction temperature and extraction time after adding 40 g of water to 10 g of spent coffee grounds.

The extraction temperature was set to 25° C. to 180° C. and the extraction time was set to 1 hour to 24 hours. Extraction yields depending on extraction temperature and extraction time are shown in FIG. 3.

Figure 3:
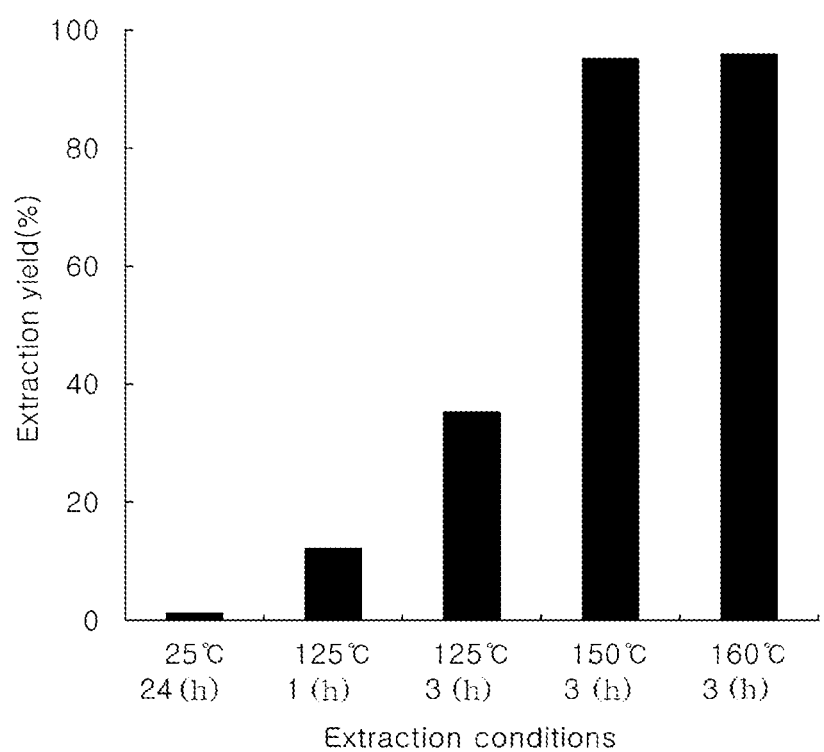
FIG. 3 is a graph depicting extraction yield when spent coffee grounds are subjected to hot water extraction at different extraction temperatures for different extraction times.

FIG. 3 is a graph depicting results of primary extraction. When spent coffee grounds were left at room temperature for 24 hours, the content of galactose was very low, and the extraction yield and extract content increased to certain levels with increasing extraction temperature and extraction time. Extraction of spent coffee grounds at 125° C. for 1 hour provided an extraction yield of about 12%, extraction of spent coffee grounds at 125° C. for 3 hours provided an extraction yield of about 35%, and extraction of spent coffee grounds at 150° C. for 3 hours and at 160° C. for 3 hours provided similar extraction yields, namely, about 95% or more. At extraction temperatures exceeding 160° C., the extraction yield remained almost unchanged. For example, at an extraction temperature of 160° C., the extraction yield remained unchanged after 1 hour.

Example 3

Acid Hydrolysis of Spent Coffee Grounds Derived Oligosaccharides 10 g of a hot water extract (obtained by adding 40 g of water to 10 g of spent coffee grounds, followed by hot water extraction at about 160° C. for 3 hours; and contained coffee derived oligosaccharides such as arabinogalactan, galactomannan) from spent coffee grounds as in Example 2 was subjected to acid hydrolysis to obtain galactose.

In the case where hot water extraction was performed by adding 40 g of water to 10 g of the spent coffee grounds, saccharide concentration was very low to a level of about 5%. In order to perform acid hydrolysis, the hot water extracted oligosaccharides were concentrated to 30 wt %.

Example 3-1

Hydrolysis Using Hydrochloric Acid

To the concentrated coffee derived oligosaccharides, a hydrochloric acid solution was added in a concentration from 0.25% to 3% (wt/v), and left at a reaction temperature of 121° C. for 1 hour to determine hydrolysis rate depending on the concentration of hydrochloric acid. After hydrochloric acid hydrolysis, precipitates were removed to collect soluble materials dissolved in the aqueous layer. To the acid hydrolyzed solution of pH 1~2, calcium carbonate was added to neutralize the reaction by adjusting pH to 6 or more, and left at room temperature for about 1 hour, thereby reacting chloride ions (Cl−) with calcium ions in the reaction solution to precipitate calcium chloride. The neutralized hydrolysate was subjected to centrifugation to harvest the supernatant, which in turn was used in evaluation of hydrolysis rate. Since the hydrolysis rate was about 97% or more in a concentration of 1% (wt/v) hydrochloric acid, the final concentration of hydrochloric acid was selected to be 1% (wt/v). In hydrolysis using sulfuric acid, the hydrolysis rate was found to be much lower (about 70%) in the same concentration.

Example 3-2

Hydrolysis Using Sulfuric Acid

To a concentrated coffee derived oligosaccharide, a sulfuric acid solution in a concentration of 0.5% to 5% (wt/v) was added, and left at a reaction temperature of 121° C. for 1 hour. After sulfuric acid hydrolysis, precipitates were removed in order to recover soluble materials dissolved in the aqueous layer. To the acid hydrolyzed solution of pH 1~2, calcium carbonate was added to neutralize the reaction by adjusting pH to 6 or more, and left at room temperature for 1 hour or so, thereby reacting chloride ions (Cl—) with calcium ions in the reaction solution to precipitate calcium chloride. The neutralized hydrolysate was subjected to centrifugation to harvest the supernatant, which in turn was used in evaluation of hydrolysis rate. The hydrolysis rate in a sulfuric acid concentration of 0.5% to 2% (wt/v) was 80% at maximum. It could be seen that the saccharide recovery rate was decreased in a concentration of 3% (wt/v) or more. Thus, the final sulfuric acid concentration was selected as 3% (wt/v).

Example 4

Hydrolysis of Spent Coffee Grounds by Adding Water Without Passing Through Hot Water Extraction To 10 g of spent coffee grounds obtained from the coffee bean product available from company B, 40 g of water was added, followed by acid hydrolysis under the same conditions as in Example 3 to obtain about 38 g of hydrolysate. The hydrolysis conditions were the same as hot water extraction in Example 3. Since the spent coffee grounds solution containing water without passing through hot water extraction had a much lower saccharide content than the hot water extracted solution (the oligosaccharide content in the extracted solution was about 30 wt %), about 95% or more of hydrolysis rate was obtained in a hydrochloric acid concentration of 0.5% (wt/v) and about 96% or more of hydrolysis rate was obtained in a sulfuric acid concentration of 1% (wt/v).

Example 5

Decoloration, Ion Refining and Chromatographic Separation of Hydrolysates

To the hydrolysate (sulfuric acid (3% wt/v) hydrolysate) prepared in Example 3, 0.5% (wt/v) of powdered activated carbon was added, followed by stirring at 100 rpm at 70° C. for 1 hour. The resulting mass was filtered to remove color materials and impurities.

In order to remove ionic impurities from the hydrolysate after decolorization, the resulting mass was passed through columns filled with a cation exchange resin substituted with a hydrogen group and an anion exchange resin substituted with a hydroxyl group in a ratio of 1:1.5 in sequence, thereby removing ionic materials from the solution such that ionic materials can be present in an amount of less than 10 microsiemens per centimeter upon measurement of electrical conductivity.

The hydrolysate having passed through decolorization and ion refining to remove impurities such as color materials and ionic materials was concentrated to 60% (g/g solution).

The refined and concentrated hydrolysates were subjected to isomerization (Example 6) without chromatography (pure galactose separation procedure) in order to minimize tagatose preparation procedures.

Separately, the refined and concentrated hydrolysate was subjected to ion exchange resin substituted with a calcium group (Amberlite CR1310 Ca), followed by elution using deionized water. The resulting solution was subjected to fractional chromatography to obtain a refined galactose solution.

Example 6

Isomerization of Spent Coffee Grounds Derived Galactose Into Tagatose

Isomerization was performed by adding a strain of *Corynebacterium glutamicum* CJ1-TNAI(KCCM10786P) in which *Thermotoga neapolitana* derived L-arabinose isomerase was expressed in a *Corynebacterium glutamicum* host to the spent coffee grounds derived galactose solution (separated solution from chromatography) or refined and concentrated hydrolysate without passing through chromatography procedures (saccharified solution containing galactose, arabinose, and the like) obtained in accordance with Example 3. Specifically, a strain of *Corynebacterium glutamicum* CJ1-TNAI (KCCM10786P) was cultured at 30° C. for 20 hours. The resulting cultured solution was centrifuged at 8000 g for 10 minutes to harvest bacterial bodies, which were resuspended in a 50 mM Tris-HCl (pH 7.5) buffer solution including 5 mM $MnCl_2$. The suspended bacterial bodies (final concentration: 30%) were reacted using the spent coffee grounds derived galactose solution or the refined hydrolysate as substrates (substrate concentration: 30%) at 70° C. for 3 hours to obtain 31.8 g/L of tagatose isomerized from the spent coffee derived galactose (in the case where galactose solution was used as a substrate) and 31.2 g/L of tagatose (in the case where refined hydrolysate was used as a substrate). As a result, it is possible to secure low cost and steadily suppliable raw materials for tagatose.

Deposition Number
Depositary Authority: Korea Culture Center of Microorganisms (KCCM)
Accession number: KCCM10786P
Date of deposit: Oct. 18, 2006

The invention claimed is:

1. A method for producing tagatose, the method comprising:
   providing spent coffee grounds or an extract therefrom containing oligosaccharides that comprise arabinogalactan and galactomannan,
   contacting the spent coffee grounds or the extract with an acid to hydrolyze oligosaccharides contained therein to produce galactose in a hydrolysate,
   subjecting the hydrolysate to decolorization and ion refining to provide a decolored and refined composition, and
   subjecting the decolored and refined composition to an isomerization reaction of galactose contained therein with an L-arabinose isomerase to produce tagatose.

2. The method according to claim 1, wherein providing the extract comprises subjecting spent coffee grounds to hot water extraction.

3. The method according to claim 2, wherein the hot water extraction comprises:
   adding water to the spent coffee grounds in an amount of 2 to 6 times the weight of the spent coffee grounds, and
   then maintaining a mixture of the water and the spent coffee grounds at a temperature of 25° C. to 180° C. for 1 hour to 24 hours.

4. The method according to claim 1, wherein the spent coffee grounds have an arabinose content that is less than 10 wt % based on the total saccharide content contained therein.

5. The method according to claim 3, wherein the acid is in an amount of 0.25 wt % to 10 wt % based on the total amount of the mixture, and wherein contacting with the acid is performed at a temperature of 100° C. to 150° C. for 1 minute to 6 hours.

6. The method according to claim 5, wherein the acid hydrochloric acid, sulfuric acid or nitric acid.

7. The method according to claim 1, wherein the decolorization comprises adding, to the hydrolysate, activated carbon in an amount of 0.1 wt % to 5.0 wt % based on the total amount of the hydrolysate at a temperature of 15° C. to 100° C.

8. The method according to claim 7, wherein the decolorization is performed while stirring the hydrolysate at a stirring rate of 10 rpm to 1000 rpm for 5 minutes to 6 hours.

9. The method according to claim 1, wherein the ion refining is performed using a cation exchange resin, an anion exchange resin or both cation and anion exchange resins.

10. The method according to claim 1, wherein the L-arabinose isomerase is an enzyme obtained from hyperthermophiles.

11. The method according to claim 1, wherein the L-arabinose isomerase is an enzyme obtained from *Thermotoga neapolitana*.

12. The method according to claim 1, wherein the isomerization reaction comprises causing the decolored and refined composition to contact a strain expressing L-arabinose isomerase at a temperature of 40° C. to 90° C. for 1 hour to 12 hours.

13. The method according to claim 12, wherein the strain expressing L-arabinose isomerase is *Corynebacterium glutamicum*.

14. The method according to claim 13, wherein the strain is *Corynebacterium glutamicum* KCCM10786P.

15. A method for producing tagatose, the method comprising:
   providing spent coffee grounds or an extract therefrom containing oligosaccharides that comprise arabinogalactan and galactomannan,
   contacting the spent coffee grounds or the extract with an acid to hydrolyze oligosaccharides contained therein to produce galactose in a hydrolysate,
   subjecting the hydrolysate to decolorization and ion refining to provide a decolored and refined composition containing galactose,
   separating the galactose from the decolored and refined composition; and
   subjecting the separated galactose to an isomerization reaction with an L-arabinose isomerase to produce tagatose.

16. The method according to claim 15, wherein providing spent coffee grounds comprises selecting spent coffee grounds containing arabinose at a concentration less than 10 wt % with reference to the total saccharide contained therein, wherein arabinose exists in the form of arabinogalactan.

17. The method according to claim 15, wherein providing the extract comprises subjecting the spent coffee grounds to hot water extraction.

18. The method according to claim 17, wherein the hot water extraction comprises adding water to the spent coffee grounds in an amount of 2 to 6 times the weight of the spent coffee grounds, and then maintaining a mixture of the water and the spent coffee grounds at a temperature of 25° C. to 180° C. for 1 hour to 24 hours.

19. The method according to claim 15, wherein the isomerization reaction comprises causing the decolored and refined composition to contact a strain expressing L-arabinose isomerase.

20. The method according to claim 19, wherein the strain is *Corynebacterium glutamicum* KCCM10786P.

* * * * *

UNITED STATES PATENT AND TRADEMARK OFFICE
CERTIFICATE OF CORRECTION

PATENT NO. : 9,879,296 B2  
APPLICATION NO. : 15/100284  
DATED : January 30, 2018  
INVENTOR(S) : Young Mi Lee et al.

Page 1 of 1

It is certified that error appears in the above-identified patent and that said Letters Patent is hereby corrected as shown below:

At Column 4, Line 17, change "Staphylococus" to --Staphylococcus--.

At Column 11, Line 38, in Claim 6, after "acid" insert --is--.

Signed and Sealed this  
Fifteenth Day of May, 2018

Andrei Iancu  
*Director of the United States Patent and Trademark Office*